US007638658B2

United States Patent
Bonrath et al.

(10) Patent No.: US 7,638,658 B2
(45) Date of Patent: Dec. 29, 2009

(54) ETHYNYLATION PROCESS

(75) Inventors: Werner Bonrath, Freiburg (DE); Peter Scheer, Visp (CH); Johannes Tschumi, Baltschieder (CH); Reto Zenhaeusern, Baltschieder (CH)

(73) Assignee: DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 10/524,762

(22) PCT Filed: Aug. 9, 2003

(86) PCT No.: PCT/EP03/08867

§ 371 (c)(1),
(2), (4) Date: Feb. 15, 2005

(87) PCT Pub. No.: WO2004/018400

PCT Pub. Date: Mar. 4, 2004

(65) Prior Publication Data

US 2005/0240066 A1 Oct. 27, 2005

(30) Foreign Application Priority Data

Aug. 16, 2002 (EP) .................. 02018458

(51) Int. Cl.
*C07C 33/04* (2006.01)
*C07C 33/042* (2006.01)
*C07C 33/28* (2006.01)

(52) U.S. Cl. .................. 568/874; 568/813

(58) Field of Classification Search ............ 568/867, 568/876

See application file for complete search history.

(56) References Cited

U.S. PATENT DOCUMENTS

| 3,082,260 | A | * | 3/1963 | Tedeschi et al. | ............. 568/874 |
| 3,283,014 | A | * | 11/1966 | Balducci et al. | ............. 568/874 |
| 3,383,427 | A | * | 5/1968 | Wolfe | ........................ 568/873 |
| 3,709,946 | A | * | 1/1973 | Tedeschi et al. | ............. 568/700 |
| 2002/0183565 | A1 | | 12/2002 | Ansmann et al. | |
| 2007/0191649 | A1 | * | 8/2007 | Klass et al. | ................. 568/879 |

FOREIGN PATENT DOCUMENTS

| EP | 1 256 560 A2 | 11/2002 |
| FR | 2 236 822 | 2/1975 |

OTHER PUBLICATIONS

Tedeschi, R.J. et al., "Base-Catalyzed Reaction of Acetylene and Vinylacetylenes with Carbonyl Compounds in Liquid Ammonia under Pressure," *J. Org. Chem.*, vol. 28, pp. 1740-1743 (1963).
Derwent Database, English language abstract of FR 2 236 822 (document B2 above), (copyright 2005).

* cited by examiner

*Primary Examiner*—Brian J Davis
(74) *Attorney, Agent, or Firm*—Hoxie & Associates LLC

(57) ABSTRACT

A process for the manufacture of an acetylenically unsaturated alcohol comprising reacting formaldehyde, an aldehyde or a ketone (a carbonyl compound) with acetylene in the presence of ammonia and an alkali metal hydroxide, the molar ratio of the alkali metal hydroxide to the carbonyl compound being less than 1:200. The reaction products, which depending on the starting carbonyl compound are propargyl alcohol or 1-monosubstituted or 1,1-disubstituted derivatives thereof, are of use as intermediates in the synthesis of many useful end products, inter alia in the field of vitamins and carotenoids.

31 Claims, No Drawings

ETHYNYLATION PROCESS

This application is the National Stage of International Application No. PCT/EP2003/008867, filed Aug. 9, 2003.

The present invention relates to an ethynylation process. More particularly, the present invention relates to a process for the manufacture of acetylenically unsaturated alcohols (propargyl alcohol or 1-monosubstituted or 1,1-disubstituted derivatives thereof) in which process formaldehyde, an aldehyde other than formaldehyde, or a ketone, each of these being referred to hereinafter in general as a "carbonyl compound", is reacted with acetylene (ethyne) in the presence of ammonia and an alkali metal hydroxide wherein the molar ratio of the alkali metal hydroxide to the carbonyl compound is less than 1:200.

The reaction products are of use as intermediates in the synthesis of many useful end products, inter alia in the field of vitamins and carotenoids. For example, one such useful intermediate is dehydrolinalool, which itself can be converted via citral to β-ionone and isophytol, themselves being known starting materials for vitamin A and vitamin E, respectively.

The manufacture of acetylenically unsaturated alcohols by reaction of a ketone with acetylene in the presence of ammonia and an alkali metal hydroxide is known for example from German Auslegeschrift (DAS) 1 232 573. According to this patent publication the ethynylation reaction is carried out at a temperature of from −40° C. to +40° C. in the presence of an alkali metal hydroxide, the molar ratio of the allali metal hydroxide to the ketone being from 1:10 to 1:200. As is apparent from technical data provided in DAS 1 232 573 the yield of the ethynylation product decreases when the relative amount of the alkali metal hydroxide is reduced.

It has now been surprisingly found that acetylenically unsaturated alcohols can be obtained in superior yields within short reaction times by reacting the appropriate carbonyl compound with acetylene in the presence of ammonia and an alkali metal hydroxide when the molar ratio of the alkali metal hydroxide to the carbonyl compound is less than 1:200, i.e. the ratio is 1:>200. The use of such low amounts of alkali metal hydroxide, i.e. much lower relative amounts than the amounts usable according to the teachings of DAS 1 232 573, not only reduces the amount of salt to be disposed of as waste by-product, but also surprisingly results in a reduced formation of diol by-product. Since in the previously known ketone acetylations the formation of diol by-products tends to increase as the temperature is elevated the reaction in accordance with the present invention can be carried out at higher temperatures, i.e. without cooling, while still keeping the diol by-product formation at low levels.

Accordingly, the present invention provides a process for the manufacture of an acetylenically unsaturated alcohol comprising reacting formaldehyde, an aldehyde or a ketone (a carbonyl compound) with acetylene in the presence of ammonia and an alkali metal hydroxide, characterized in that the molar ratio of the alkali metal hydroxide to the carbonyl compound is less than 1:200.

The simplest carbonyl compound which can be reacted with acetylene in accordance with the process of the present invention is formaldehyde, HCHO, the product being propargyl alcohol, HC≡CCH₂OH.

The nature of any other aldehyde or of the ketone which can be reacted with acetylene in accordance with the process of the present invention is not critical, and any aldehyde or ketone with which acetylene is known to react to form an acetylenically unsaturated alcohol may be used, i.e. according to the equation

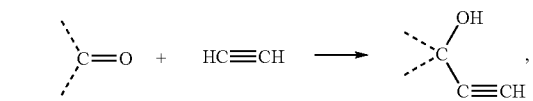

the unspecified moieties attached to the "central" carbon atom by the dotted lines being those featured in known aldehydes and ketones or in any other aldehydes and ketones which can be produced analogously to the known ones. Thus, for example, the aldehyde, including formaldehyde, or ketone may be one of those of formula "R⁵—CO—R⁶" as defined in German Offenlegungsschrift (DOS) 2 018 971, the contents of which are incorporated herein for reference purposes. Preferably, the starting carbonyl compound is a ketone of the general formula

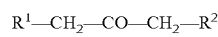   I wherein each of $R^1$ and $R^2$, independently, signifies hydrogen, alkyl, alkenyl, cycloalkyl-alkyl, cycloalkyl-alkenyl, cycloalkenyl-alkyl or cycloalkenyl-alkenyl, each of the last four mentioned groups being optionally substituted on its cycloalkyl or cycloalkenyl ring, as appropriate, by one to three methyl or ethyl groups, the total number of carbon atoms, including those of the —CH₂—CO—CH₂— moiety, not exceeding 40.

In the above definition of the ketones of the general formula I an alkyl group signified by $R^1$ and/or $R^2$ suitably contains up to 22 carbon atoms and may be straight chain or branched, which also applies to the alkenyl group. Said alkenyl group, in addition, may feature up to 4 double bonds. The cycloalkyl-alkyl, cycloalkenyl-alkyl, cycloalkyl-alkenyl or cycloalkenyl-alkenyl group signified by $R^1$ and/or $R^2$ features a cycloaucyl or cycloalkenyl ring, as appropriate, which has from 5 to 12 ring members; the alkyl or alkenyl part of such group can contain from 1 to 8 carbon atoms and be straight chain or branched, and in the case of alkenyl as part of such group this can feature up to 4 double bonds. Furthermore, and as also indicated in the definition of formula I, the cycloalkyl or cycloalkenyl ring part of such groups is either unsubstituted or is substituted by one, two or three methyl or ethyl groups, whereby in the case of di- or trisubstitution the substituents can be the same (methyl or ethyl) or different (a mixture of methyl and ethyl substituents). A particularly preferred optionally substituted cycloalkenyl group (as part of cycloalkenyl-alkyl or cycloalkenyl-alkenyl) is the well known 2,6,6-trimethyl-1-cyclohexen-1-yl group.

Clearly, the total number of carbon atoms, including any ring methyl or ethyl substituent(s), if appropriate, of either $R^1$ or $R^2$ is limited by that of the remaining $R^2$ or $R^1$, respectively, to satisfy the criterion of the molecule $R^1$—CH₂—CO—CH₂—$R^2$ as a whole containing a maximum of 40 carbon atoms.

Of particular interest is the process of the present invention when applied to the ethynylation of methyl ethyl ketone (2-butanone), 6-methyl-5-hepten-2-one, 6-methyl-5-octen-2-one, 6,10-dimethyl-2-undecanone (hexahydropseudoionone), 4-(2,6,6-trimethyl-1-cyclohexen-1-yl)-3-buten-2-one and 6,10,14-trimethyl-2-pentadecanone (all ketones of formula I), and also to the ethynylation of methylglyoxal dimethylacetal [CH₃COCH(OCH₃)₂], not a ketone of the formula I, but nonetheless a ketone amongst many others which can be reacted with acetylene in accordance with the process of the present invention. Of these specifically named ketones 6-methyl-5-hepten-2-one is a particularly preferred ketone which can be reacted with acetylene by the process of the present invention; the product in this case is 3,7-dimethyl-6-octen-1-yn-3-ol (dehydrolinalool).

As the alkali metal hydroxide used as the basic catalyst in the process of the present invention there may be used sodium hydroxide or potassium hydroxide, of which the latter is preferably used.

The ammonia used as the solvent in the process of the present invention is maintained in the liquid state by appropriate choice of temperature and pressure, whereby at the same time an adequate acetylene pressure must also be provided and sustained in the reaction vessel. The reaction temperature is conveniently in the range from about 0° C. to about 40° C. The pressure is maintained at an appropriate value, depending on the reaction temperature, which is suitably from about 5 bar to about 20 bar (about 0.5 MPa to about 2 MPa). By using liquefied ammonia as the reaction solvent, the process of the present invention avoids the use of organic solvents, which is one of its advantages.

The ethynylation is preferably effected at temperatures from about room temperature (about 20° C.) to about 35° C.

The molar ratio of the acetylene to the formaldehyde, aldehyde or ketone (carbonyl compound), e.g. a ketone of the formula I, in the reaction mixture for carrying out the process of the present invention is generally from about 2:1 to about 6:1. Furthermore, the molar ratio of ammonia to carbonyl compound in said process is generally from about 8:1 to about 35:1, preferably from about 10:1 to about 30:1.

Characteristic of the process of the present invention is the relatively extremely small amount of alkali metal hydroxide used as the basic catalyst, i.e. the molar ratio of alkali metal hydroxide to carbonyl compound being less than 1:200 (1:>200). The ratio range within which the inventive process is effected is conveniently from about 1:500 to about 1:200, preferably from about 1:300 to about 1:220.

The process of the present invention can be carried out in a manner known per se for the ethynylation of carbonyl compounds. Typically, for batchwise operation, the desired amounts of aqueous alkali metal hydroxide solution, the carbonyl compound and acetylene are introduced into a reactor. The reactor is then sealed and inertized by repeatedly filling with ammonia and venting. Finally, a desired amount of ammonia is introduced into the reactor. Acetylene is then also added in the desired amount with stirring to start the reaction. During the reaction further acetylene may be added semicontinuously to maintain a constant ketone: acetylene molar ratio.

Alternatively the process in accordance with the present invention can be carried out continuously, e.g. by continuous addition of a mixture of acetylene and ammonia together with the carbonyl compound and aqueous alkali hydroxide solution into a reactor, e.g. a plug-flow reactor, and continuous withdrawal of the product. The process of the present invention is preferably effected in a continuous manner.

The following Examples illustrate the process of the present invention.

EXAMPLE 1

Ethynylation of 6-methyl-5-hepten-2-one to produce 3,7-dimethyl-6-octen-1-yn-3-ol 796 mg of potassium hydroxide (KOH) in 45% (wt./vol.) aqueous solution and 194.5 g of 6-methyl-5-hepten-2-one (MH) were introduced into a reactor; the molar ratio KOH:MH was thus 1:250. After fourfold evacuation of the air from the reactor and subsequent flushing with nitrogen (inertisation of the reactor), 369 g of ammonia were introduced. Acetylene was then added to provide a pressure of 16.1 bar (1.61 MPa) at 30° C., corresponding to 21% (wt./vol.) of acetylene in the mixture of ammonia and acetylene. The contents of the reactor were agitated by gas stirring. Samples were taken at various time intervals for analysis of their content by gas chromatography (GC). After 5 hours the reaction was finally stopped since by then it had been established that a predominant amount of the desired product, 3,7-dimethyl-6-octen-1-yn-3-ol (dehydrolinalool; DLL) and only small amounts of diol by-product and unchanged MH were present. The results are presented in Table 1 below:

TABLE 1

| Product composition vs. time [minutes (min.)/hour(s) (hr./hrs.)] | | | | |
|---|---|---|---|---|
| | 5 min. | 1 hr. | 2 hrs. | 5 hrs. |
| MH | 29.2 | 4.1 | 2.5 | 2.3 |
| DLL | 67.6 | 92.9 | 94.3 | 94.1 |
| Diol | 1.0 | 1.4 | 1.5 | 1.7 |

EXAMPLE 2

Ethynylation of 6,10-dimethyl-2-undecanone to produce 3,7,11-trimethyl-1-dodecyn-3-ol In analogy to Example 1, 387 mg of potassium hydroxide in 45% (wt./vol.) aqueous solution, 153.8 g of 6,10-dimethyl-2-undecanone (hexahydropseudoionone; HPI), 360 g of ammonia, and acetylene were reacted at 16.3 bar (1.63 MPa) and 30° C.; the molar ratio KOH:HPI was thus 1:250. After 5 hours it was established by GC that a predominant amount of the desired product, 3,7,11-trimethyl-1-dodecyn-3-ol ($C_{15}$-acetylenic alcohol; $C_{15}$-AA) and only small amounts of diol by-product and unchanged HPI were present. The results are presented in Table 2 below:

TABLE 2

| Product composition vs. time | | | | |
|---|---|---|---|---|
| | 5 min. | 1 hr. | 2 hrs. | 5 hrs. |
| HPI | 29.4 | 4.0 | 3.1 | 3.1 |
| $C_{15}$-AA | 68.5 | 93.7 | 94.2 | 94.4 |
| Diol | 0.4 | 0.6 | 0.6 | 0.8 |

EXAMPLE 3

Ethynylation of 6,10,14-trimethyl-2-pentadecanone to produce 3,7,11,15-tetramethyl-1-hexadecyn-3-ol In analogy to Example 1, 358 mg of potassium hydroxide in 45% (wt./vol.) aqueous solution, 192.3 g of 6,10,14-trimethyl-2-pentadecanone ($C_{18}$-ketone), 351 g of ammonia, and acetylene were reacted at 16.8 bar (1.68 MPa) and 30° C.; the molar ratio KOH: $C_{18}$-ketone was thus 1:250. After 5 hours it was established by GC that a predominant amount of the desired product, 3,7,11,15-tetramethyl-1-hexadecyn-3-ol (dehydroisophytol; DIP) and only small amounts of diol by-product and unchanged $C_{18}$-ketone were present. The results are presented in Table 3 below:

TABLE 3

| Product composition vs. time | | | | |
|---|---|---|---|---|
| | 5 min. | 1 hr. | 2 hrs. | 5 hrs. |
| $C_{18}$-ketone | 32.7 | 4.3 | 3.1 | 2.6 |
| DIP | 64.7 | 93.3 | 94.2 | 94.5 |
| Diol | 0.4 | 0.6 | 0.6 | 0.8 |

EXAMPLE 4

Ethynylation of 6-methyl-5-octen-2-one to produce 3,7-dimethyl-6-nonen-1-yn-3-ol In analogy to Example 1, 593 mg of potassium hydroxide in 45% (wt./vol.) aqueous solution, 166.8 g of 6-methyl-5-octen-2-one (MO), 381 g of ammonia, and acetylene were reacted at 16.1 bar (1.61 MPa) and 30° C.; the molar ratio KOH:MO was thus 1:250. After 5 hours it was established by GC that a predominant amount of the desired product, 3,7-dimethyl-6-nonen-1-yn-3-ol ("ethyl dehydrolinalool"-; EDLL) and only small amounts of diol by-product and unchanged MO were present. The results are tabulated in Table 4 below:

TABLE 4

| Product composition vs. time | | | | |
|---|---|---|---|---|
| | 5 min. | 1 hr. | 2 hrs. | 5 hrs. |
| MO | 29.2 | 3.5 | 2.3 | 2.3 |
| EDLL | 68.3 | 93.9 | 95.0 | 95.0 |
| Diol | 0.5 | 0.8 | 0.9 | 1.1 |

EXAMPLE 5

Ethynylation of methyl ethyl ketone to produce 2-ethyl-3-butyn-2-ol

In analogy to Example 1, 740 mg of potassium hydroxide in 45% (wt./vol.) aqueous solution), 153.7 g of methyl ethyl ketone (MEK), 388 g of ammonia, and acetylene were reacted at 16.0 bar (1.60 MPa) and 30° C.; the molar ratio KOH:MEK was thus 1:359. Already after 1 hour it was established by GC that a predominant amount of the desired product, 2-ethyl-3-butyn-2-ol (EB) and only small amounts of diol by-product and unchanged MEK were present. The results are presented in Table 5 below:

TABLE 5

| Product composition vs. time | | |
|---|---|---|
| | 5 min. | 1 hr. |
| MEK | 25.8 | 2.9 |
| EB | 73.6 | 96.3 |
| Diol | 0.3 | 0.4 |

The invention claimed is:

1. A process for the manufacture of an acetylenically unsaturated alcohol comprising reacting a carbonyl compound with acetylene in the presence of ammonia and an alkali metal hydroxide, wherein the carbonyl compound is selected from a group consisting of methyl ethyl ketone, methylglyoxal dimethylacetal, 6-methyl-5-hepten-2-one, 6-methyl-5-octen-2-one, hexahydropseudoionone, 4-(2,6,6-trimethyl-1-cyclohexen-1-yl)-3-buten-2-one and 6,10,14-trimethyl-2-pentadecanone, the alkali metal hydroxide is used in aqueous solution and the molar ratio of the alkali metal hydroxide to the carbonyl compound is less than 1:200.

2. A process according to claim 1, wherein the molar ratio of the alkali metal hydroxide to the carbonyl compound is from about 1:500 to 1:200.

3. A process according to claim 2, wherein the molar ratio of the alkali metal hydroxide to the carbonyl compound is from about 1:300 to about 1:220.

4. A process according to claim 1, wherein the carbonyl compound is 6-methyl-5-hepten-2-one and the product is dehydrolinalool.

5. A process according to claim 1, wherein the alkali metal hydroxide is potassium hydroxide.

6. A process according to claim 1, wherein the reaction is effected at a temperature from about 0° C. to about 40° C. and the pressure is at an appropriate value, depending on the reaction temperature, from about 5 bar to about 20 bar (about 0.5 MPa to about 2 MPa) to maintain the ammonia in the liquefied state.

7. A process according to claim 6, wherein the reaction is effected at a temperature from about room temperature to about 35° C.

8. A process according to claim 1, wherein the molar ratio of the acetylene to the carbonyl compound in the reaction mixture for carrying out the process is from about 2:1 to about 6:1.

9. A process according to claim 1, wherein the molar ratio of ammonia to carbonyl compound in the reaction mixture for carrying out the process is from about 8:1 to about 35:1.

10. A process according to claim 9, wherein the molar ratio of ammonia to carbonyl compound in the reaction mixture for carrying out the process is from about 10:1 to about 30:1.

11. A process according to claim 1, wherein the reaction is effected in a continuous manner.

12. A process according to claim 4, wherein the alkali metal hydroxide is potassium hydroxide.

13. A process according to claim 4, wherein the reaction is effected at a temperature from about 0° C. to about 40° C. and the pressure is at an appropriate value, depending on the reaction temperature, from about 5 bar to about 20 bar (about 0.5 MPa to about 2 MPa) to maintain the ammonia in the liquefied state.

14. A process according to claim 5, wherein the reaction is effected at a temperature from about 0° C. to about 40° C. and the pressure is at an appropriate value, depending on the reaction temperature, from about 5 bar to about 20 bar (about 0.5 MPa to about 2 MPa) to maintain the ammonia in the liquefied state.

15. A process according to claim 12, wherein the reaction is effected at a temperature from about 0° C. to about 40° C. and the pressure is at an appropriate value, depending on the reaction temperature, from about 5 bar to about 20 bar (about 0.5 MPa to about 2 MPa) to maintain the ammonia in the liquefied state.

16. A process according to claim 4, wherein the molar ratio of the acetylene to the carbonyl compound in the reaction mixture for carrying out the process is from about 2:1 to about 6:1.

17. A process according to claim 5, wherein the molar ratio of the acetylene to the carbonyl compound in the reaction mixture for carrying out the process is from about 2:1 to about 6:1.

18. A process according to claim 4, wherein the reaction is effected in a continuous manner.

19. A process according to claim 5, wherein the reaction is effected in a continuous manner.

20. A process according to claim 12, wherein the reaction is effected in a continuous manner.

21. A process for the manufacture of an acetylenically unsaturated alcohol comprising reacting a carbonyl compound with acetylene in the presence of ammonia and an alkali metal hydroxide, wherein the alkali metal hydroxide is used in aqueous solution and the molar ratio of the alkali metal hydroxide to the carbonyl compound is less than 1:200.

22. A process according to claim 21, wherein the molar ratio of the alkali metal hydroxide to the carbonyl compound is from about 1:500 to 1:200.

23. A process according to claim 22, wherein the molar ratio of the alkali metal hydroxide to the carbonyl compound is from about 1:300 to about 1:220.

24. A process according to claim 21, wherein the carbonyl compound is a ketone of the general formula

$$R^1-CH_2-CO-CH_2-R^2 \qquad I$$

wherein each of $R^1$ and $R^2$, independently, signifies hydrogen, alkyl, alkenyl, cycloalkyl-alkyl, cycloalkyl-alkenyl, cycloalkenyl-alkyl or cycloalkenyl-alkenyl, each of the last four mentioned groups being optionally substituted on its cycloalkyl or cycloalkenyl ring, as appropriate, by one to three methyl or ethyl groups, the total number of carbon atoms, including those of the —CH$_2$—CO—CH$_2$— moiety, not exceeding 40.

25. A process according to claim 21, wherein the alkali metal hydroxide is potassium hydroxide.

26. A process according to claim 21, wherein the reaction is effected at a temperature from about 0° C. to about 40° C. and the pressure is at an appropriate value, depending on the reaction temperature, from about 5 bar to about 20 bar (about 0.5 MPa to about 2 MPa) to maintain the ammonia in the liquefied state.

27. A process according to claim 26, wherein the reaction is effected at a temperature from about room temperature to about 35° C.

28. A process according to claim 21, wherein the molar ratio of the acetylene to the carbonyl compound in the reaction mixture for carrying out the process is from about 2:1 to about 6:1.

29. A process according to claim 21, wherein the molar ratio of ammonia to carbonyl compound in the reaction mixture for carrying out the process is from about 8:1 to about 35:1.

30. A process according to claim 29, wherein the molar ratio of ammonia to carbonyl compound in the reaction mixture for carrying out the process is from about 10:1 to about 30:1.

31. A process according to claim 21, wherein the reaction is effected in a continuous manner.

* * * * *